United States Patent [19]

Buchecker et al.

[11] Patent Number: 5,102,578

[45] Date of Patent: Apr. 7, 1992

[54] LIQUID CRYSTALLINE MIXTURES AND METHOD OF MAKING SAME

[75] Inventors: Richard Buchecker, Zurich; Martin Schadt, Seltisberg; Alois Villiger, Basel, all of Switzerland

[73] Assignee: Hoffmann-La Roche Inc., Nutley, N.J.

[21] Appl. No.: 389,095

[22] Filed: Aug. 3, 1989

[30] Foreign Application Priority Data

Aug. 15, 1988 [CA] Canada .................. 3057/88
May 18, 1989 [CA] Canada .................. 1906/89

[51] Int. Cl.$^5$ .................. C09K 19/30; C09K 19/52
[52] U.S. Cl. .................. 252/299.63; 252/299.01; 568/579; 359/103
[58] Field of Search .................. 252/299.01, 299.63; 359/103; 568/579

[56] References Cited

U.S. PATENT DOCUMENTS

| | | |
|---|---|---|
| 4,507,222 | 3/1985 | Inoue et al. . |
| 4,565,425 | 1/1986 | Petrzilka et al. . |
| 4,621,901 | 11/1986 | Petrzilka et al. . |
| 4,622,164 | 11/1986 | Eidenschink et al. . |
| 4,629,581 | 12/1986 | Petrzilka et al. . |
| 4,676,604 | 6/1987 | Petrzilka . |
| 4,704,228 | 11/1987 | Inoue et al. . |
| 4,709,030 | 11/1987 | Petrzilka et al. . |
| 4,868,341 | 9/1989 | Eidenschink et al. . |

FOREIGN PATENT DOCUMENTS

| | | |
|---|---|---|
| 58981 | 9/1982 | European Pat. Off. . |
| 3601452 | 7/1987 | Fed. Rep. of Germany . |
| 59-70624 | 4/1984 | Japan . |
| 59-98053 | 6/1984 | Japan . |
| 60-69049 | 4/1985 | Japan . |
| 61-27928 | 2/1986 | Japan . |
| 61-257935 | 11/1986 | Japan . |

Primary Examiner—Robert L. Stoll
Assistant Examiner—Shean C. Wu
Attorney, Agent, or Firm—George M. Gould; George W. Johnston; Stephen L. Malaska

[57] ABSTRACT

A compound of the formula

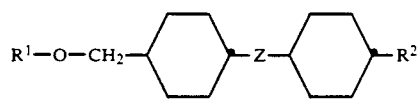

wherein Z represents a single covalent bond or —$CH_2$—$CH_2$—; $R^1$ denotes alkyl or 2-alkenyl and $R^2$ is 1E-alkenyl, 3E-alkenyl, 4-alkenyl, (2-alkenyl)oxymethyl or, when $R^1$ denotes 2-alkenyl and/or Z represents —$CH_2$—$CH_2$—, $R^2$ also is alkyl, cyano or alkoxymethyl, as well as the manufacture of the compounds of formula I. Also disclosed is the use of the compounds in liquid crystalline mixtures and for electro-optical purposes.

15 Claims, No Drawings

LIQUID CRYSTALLINE MIXTURES AND METHOD OF MAKING SAME

FIELD OF THE INVENTION

The present invention is concerned with novel alkoxymethyl and alkenyloxymethylcyclohexanes, their manufacture, liquid crystalline mixtures which contain these compounds as well as their use for electro-optical purposes.

BACKGROUND OF THE INVENTION

Liquid crystals are used primarily as dielectrics in indicating devices, since the optical properties of such substances can be influenced by an applied voltage. Electro-optical devices based on liquid crystals are well-known to the person skilled in the art and can be based on various effects. Such devices are, for example, cells having dynamic scattering, DAP cells (deformation of aligned phases), guest/host cells, TN cells having a twisted nematic structure, STN cells ("supertwisted nematic"), SBE cells ("super-birefringence effect") and OMI cells ("optical mode interference"). The most common indicating devices are based on the Schadt-Helfrich effect and have a twisted nematic structure.

The liquid crystal materials must have a good chemical and thermal stability and a good stability towards electric fields and electromagnetic radiation. Further, the liquid crystal materials should have a low viscosity and in the cells should give short response times, low threshold potentials and a high contrast. Furthermore, at the usual operating temperatures, that is, in a widest possible range below and above room temperature, they should have a suitable mesophase, for example a nematic or cholesteric mesophase for the aforementioned cells. Since liquid crystals are generally used as mixtures of several components, it is important that the components have a good miscibility with one another. Other properties such as the electrical conductivity, the dielectric anisotropy and the optical anisotropy must fulfil different requirements depending on the type of cell and field of application. For example, materials for cells having a twisted nematic structure should have a positive dielectric anisotropy and an electrical conductivity which is as low as possible.

There has recently been an increased interest in materials having a low optical anisotropy, especially for actively addressed liquid crystal indicators such as MIM applications (metal-isolator-metal) or TFT applications ("thin film transistor") in television sets. However, the known liquid crystalline compounds having a low optical anisotropy frequently produce smectic tendencies in mixtures and for the most part lead to an undesired increase in the threshold potential, the viscosity and/or the response times.

SUMMARY OF THE INVENTION

The present invention provides the compounds of the formula

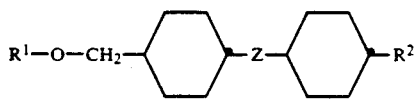

wherein Z is a single covalent bond or —CH$_2$—CH$_2$—; R$^1$ is alkyl or 2-alkenyl; and R$^2$ is 1E-alkenyl, 3E-alkenyl, 4-alkenyl, (2-alkenyl)oxymethyl, alkyl, cyano or alkoxymethyl; with the proviso that R$^1$ is 2-alkenyl or Z is —CH$_2$CH$_2$— when R$^2$ is alkyl, cyano or alkoxymethyl.

The compounds in accordance with the invention are liquid crystals having a very low optical anisotropy, relatively low melting points and for the most part comparatively high clearing points. They have a very good solubility in known liquid crystal materials and produce a good melting behavior in mixtures.

The compounds in accordance with the invention have low viscosities and produce remarkably short switching times in mixtures. In particular, the switching-on times are generally considerably shorter than those of mixtures of comparable compounds having a low optical anisotropy.

The short response times and the good melting behavior can also be passed on to complex mixtures so that rapidly switching liquid crystals having high clearing points, low melting points and at the same time low threshold potentials, short response times (especially at low temperatures) and comparatively low optical anisotropies are obtained.

These properties can be varied to a certain extent depending on the significance of R$^1$ and R$^2$. 4-Alkenyl or (2-alkenyl)oxymethyl in R$^2$ and/or 2-alkenyl in R$^1$ leads, for example, to particularly low threshold potentials and optical anisotropies. On the other hand, compounds of formula I in which R$^2$ is 1E-alkenyl or 3E-alkenyl generally give higher clearing points and shorter response times.

The compounds of formula I in which R$^2$ is cyano are novel intermediates for the manufacture of the compounds of formula I in which R$^2$ is alkoxymethyl or (2-alkenyl)-oxymethyl. They also have liquid crystalline properties, a low optical anisotropy and short response times. The cyano compounds have a positive dielectric anisotropy; the remaining compounds of formula I are non-polar compounds having a small absolute value of the dielectric anisotropy.

The compounds in accordance with the invention are especially suitable as components of nematic and cholesteric mixtures. They can be used in the usual electro-optical devices, for example in the liquid crystal cells mentioned earlier. Having regard to the low optical anisotropy, they are especially suitable for use in liquid crystal mixtures for OMI cells, for TFT applications, for TN cells, which are operated in the first minimum, and the like.

DETAILED DESCRIPTION OF PREFERRED EMBODIMENTS

The present invention provides the compounds of the formula

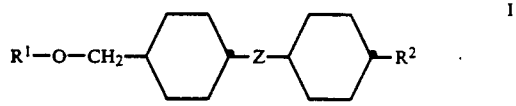

wherein Z is a single covalent bond or —CH$_2$—CH$_2$—; R$^1$ is alkyl or 2-alkenyl; and R$^2$ is 1E-alkenyl, 3E-alkenyl, 4-alkenyl, (2-alkenyl)oxymethyl, alkyl, cyano or alkoxymethyl; with the proviso that R$^1$ is 2-alkenyl or Z is —CH$_2$CH$_2$— when R$^2$ is alkyl, cyano or alkoxymethyl.

Formula I embraces the compounds of the formulas

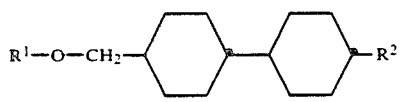
Ia wherein
R$^1$ denotes alkyl and R$^2$ denotes 1E-alkenyl, 3E-alkenyl, 4-alkenyl or (2-alkenyl)oxymethyl or
R$^1$ denotes 2-alkenyl and R$^2$ denotes 1E-alkenyl, 3E-alkenyl, 4-alkenyl, (2-alkenyl)oxymethyl, alkyl, cyano or alkoxymethyl,
and

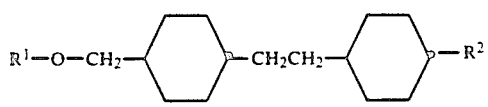
Ib wherein R$^1$ denotes alkyl and R$^2$ denotes 1E-alkenyl, 3E-alkenyl, 4-alkenyl, (2-alkenyl)oxymethyl, alkyl, cyano or alkoxymethyl or R$^1$ denotes 2-alkenyl and R$^2$ denotes 1E-alkenyl, 3E-alkenyl, 4-alkenyl, (2-alkenyl)oxymethyl, alkyl, cyano or alkoxymethyl.

The terms "alkyl", "1E-alkenyl", "2-alkenyl", "3E-alkenyl", "4-alkenyl", "alkoxymethyl" and "(2-alkenyl)oxymethyl" embrace in the scope of the present invention straight-chain and branched groups. Examples of preferred groups are methyl, ethyl, propyl, butyl (=n-butyl), s-butyl, 2-methylbutyl, pentyl (=n-pentyl), 2-pentyl, hexyl, heptyl, vinyl, 1E-propenyl, 1E-butenyl, 1E-pentenyl, 1E-hexenyl, 1E-heptenyl, allyl, 2E-butenyl, 2Z-butenyl, 2E-pentenyl, 2Z-pentenyl, 3-butenyl, 3E-pentenyl, 3E-hexenyl, 3E-heptenyl, 4-pentenyl, 4E-hexenyl, 4Z-hexenyl, 4E-heptenyl, 4Z-heptenyl, methoxymethyl, ethoxymethyl, propyloxymethyl, butyloxymethyl, s-butyloxymethyl, pentyloxymethyl, (2-pentyl)oxymethyl, (2-methylbutyl)oxymethyl, allyloxymethyl, (2E-butenyl)oxymethyl, (2Z-butenyl)oxymethyl, (2E-pentenyl)oxymethyl, (2Z-pentenyl)oxymethyl and the like. 2-Alkenyl and 4-alkenyl groups can be present in the E-configuration or preferably in the Z-configuration.

Compounds of formula I having straight-chain residues R$^1$ and R$^2$ are generally preferred. However, if desired, R$^1$ and/or R$^2$ can be branched, and branched groups can preferably be chiral. Optically active compounds of formula I having chiral R$^1$ and/or R$^2$ are suitable, for example, as optically active doping substances for the production of chlesteric mixtures or for avoiding the reversal of the twisting direction (reverse twist) in TN cells.

R$^1$ in formulas I, Ia and Ib above preferably has a maximum of 10 carbon atoms, particularly a maximum of 5 carbon atoms. Preferred residues R$^1$ are therefore C$_1$-C$_{10}$-alkyl and C$_3$-C$_{10}$-2-alkenyl, especially C$_1$-C$_5$-alkyl and C$_3$-C$_5$-2-alkenyl. Methyl, ethyl, propyl, allyl and 2-butenyl are examples of especially preferred residues R$^1$.

R$^2$ in formulas I, Ia and Ib preferably has a maximum of 12 carbon atoms, particularly a maximum of 7 carbon atoms. Preferred residues R$^2$ are therefore C$_2$-C$_{12}$-1E-alkenyl, C$_4$-C$_{12}$-3E-alkenyl, C$_5$-C$_{12}$-4-alkenyl, C$_4$-C$_{12}$-(2-alkenyl)oxymethyl, C$_1$-C$_{12}$-alkyl and C$_2$-C$_{12}$-alkoxymethyl, especially C$_2$-C$_7$-1E-alkenyl, C$_4$-C$_7$-3E-alkenyl, C$_5$-C$_7$-4-alkenyl, C$_4$-C$_7$-(2-alkenyl)oxymethyl, C$_1$-C$_7$-alkyl and C$_2$-C$_7$-aloxymethyl. Vinyl, 1E-propenyl, 1E-butenyl, 1E-pentenyl, 3-butenyl, 3E-pentenyl, 4-pentenyl, allyloxymethyl, (2-butenyl)oxymethyl, methyl, ethyl, propyl, butyl, pentyl, methoxymethyl, ethoxymethyl, propyloxymethyl and butyloxymethyl are examples of especially preferred residues R$^2$.

Compounds of formula I which have a C—C double bond in R$^1$ and/or R$^2$ are generally preferred. Accordingly, in formulas I, Ia and Ib above R$^1$ preferably stands for 2-alkenyl and/or R$^2$ preferably stands for 1E-alkenyl, 3E-alkenyl, 4-alkenyl or (2-alkenyl)oxymethyl.

The compounds of formula I can be prepared in accordance with the invention by etherifying a compound of the formula

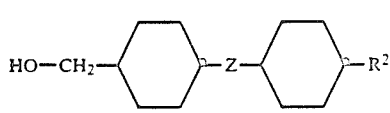
II with a compound of the formula

R$^1$-X     III wherein X denotes chlorine, bromine or iodine and R$^1$ and R$^2$ have the above significances.

The etherification can be effected in a manner known per se using usual bases. The etherification is preferably effected with the bromide or iodide of formula III.

The preparation of the compounds of formula II in which R$^2$ is cyano can be effected in a manner known per se from the corresponding cyano-aldehydes, for example by reducing the formyl group to the hydroxymethyl group with sodium borohydride.

The compounds of formula II in which R$^2$ is different from cyano can be prepared in a manner known per se from the nitriles of the formula

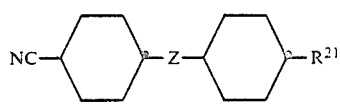
IV wherein Z represents a single covalent bond or —CH$_2$CH$_2$— and R$^{21}$ is 1E-alkenyl, 3E-alkenyl, 4-alkenyl, (2-alkenyl)oxymethyl, alkyl or alkoxymethyl, for example by hydrolyzing the cyano group and subsequently reducing the carboxy group to the hydroxymethyl group. Preferably, the hydrolysis and reduction can be effected according to the methods described in the Examples hereinafter.

The compounds of formula IV in which Z is a single covalent bond and R$^{21}$ is (2-alkenyl)oxy- methyl or Z is —CH$_2$CH$_2$— and R$^{21}$ is alkoxymethyl or (2-alkenyl)oxymethyl are novel compounds and are embraced by formula I above. They can be prepared according to the methods described above.

The compounds of formula I can be used in the form of mixtures with one another and/or with other liquid crystal components such as for example, with substances from the classes of Schiff's bases, azobenzenes, azoxybenzenes, phenylbenzoates, cyclohexanecarboxylic acid phenyl esters, cyclohexanecarboxylic acid cyclohexyl esters, biphenyls, phenylcyclohexanes, cyclohexylcyclohexanes, phenylpyrimidines, cyclohexylpyrimidines, phenyldioxanes, 2-cyclohexyl-1-phenylethanes, terphenyls, cyclohexylbiphenyls, cyclohexylphenylpyrimidines and the like. Such substances are known to the person skilled in the art and many of them are, moreover, commercially available.

The liquid crystalline mixtures in accordance with the invention contain at least two components, of which at least one component is a compound of formula I. A second component and optionally further components can be further compounds of formula I and/or other liquid crystal components.

The compounds of formula I are especially suitable for nematic mixtures or, insofar as at least one component of the mixture is optically active, also for cholesteric mixtures. A preferred field of application is their use as dielectrics in liquid crystal indicating devices having a twisted nematic liquid crystal structure such as TN cells, STN cells, SBE cells and OMI cells. Preferred mixtures are therefore those which contain one or more compounds of formula I and one or more compounds having positive dielectric anisotropy.

Having regard to the good solubility of the compounds of formula I in other liquid crystal materials and having regard to their good miscibility with one another, the amount of compounds of formula I in the mixtures in accordance with the invention can be relatively high and can amount to, for example, about 1-70 wt. %. An amount of about 3-40 wt. %, especially about 5-30 wt. %, of compounds of formula I is generally preferred.

The mixtures in accordance with the invention preferably contain, in addition to one or more compounds of formula I, one or more compounds from the group of compounds of the formulas

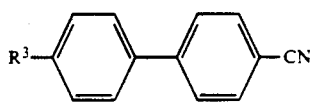
V

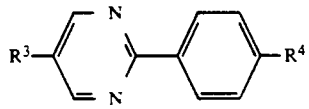
VI

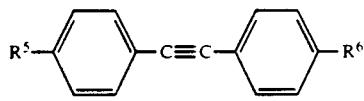
VII

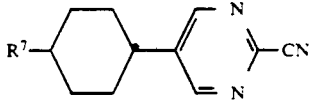
VIII

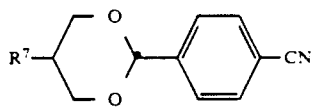
IX

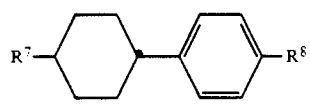
X

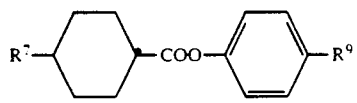
XI

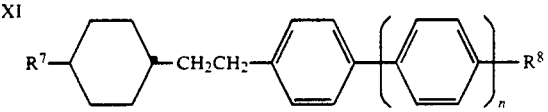
XII

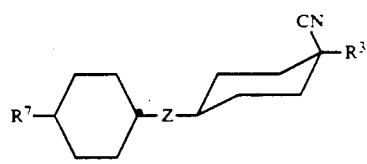
XIII

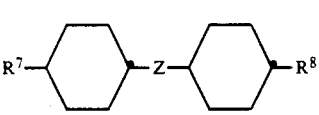
XIV

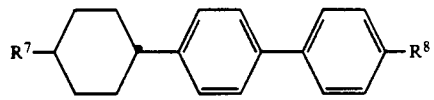
XV

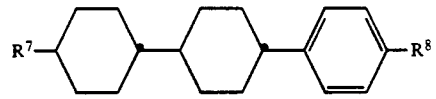
XVI

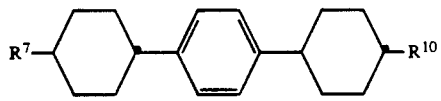
XVII

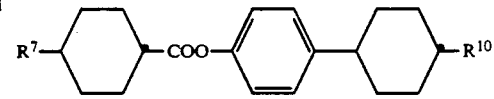
XVIII

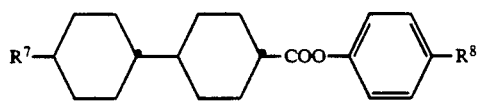
XIX

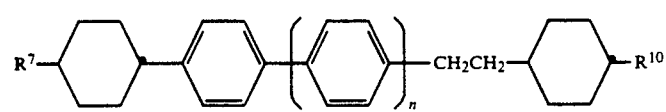
XX

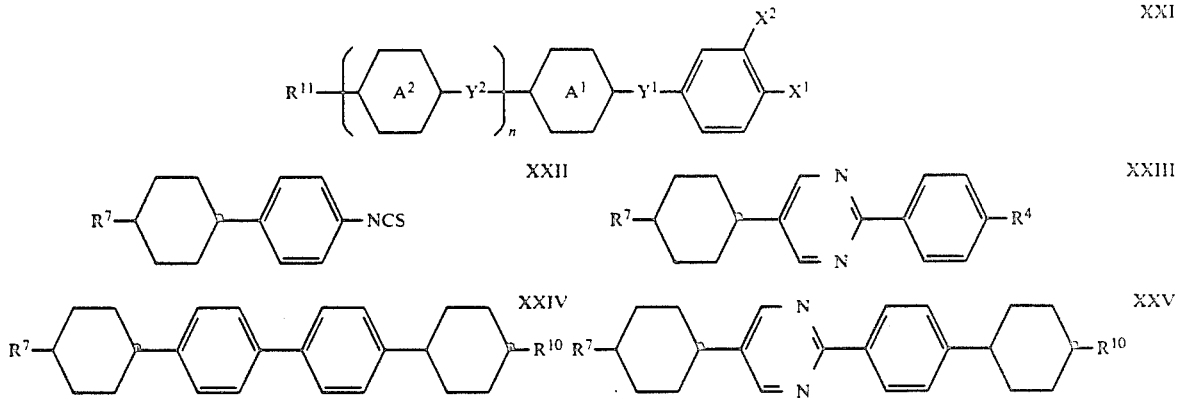

wherein $R^3$ is alkyl, 3E-alkenyl or 4-alkenyl; $R^4$ represents alkyl, cyano or fluorine; $R^5$ and $R^6$ denote alkyl or alkoxy; $R^7$ and $R^{10}$ each independently are alkyl, 1E-alkenyl, 3E-alkenyl or 4-alkenyl; $R^8$ denotes cyano, alkyl, 1E-alkenyl, 3E-alkenyl, 4-alkenyl, alkoxy, 2E-alkenyloxy or 3-alkenyloxy; $R^9$ is alkoxy, 2E-alkenyloxy or 3-alkenyloxy; n stands for the number 0 or 1; Z represents a single covalent bond or —$CH_2CH_2$—; $X^1$ denotes fluorine or chlorine and $X^2$ denotes hydrogen, fluorine or chlorine: $R^{11}$ is alkyl, 3E-alkenyl, 4-alkenyl, alkoxy, 2E-alkenyloxy or 3-alkenyloxy; one of the groups $Y^1$ and $Y^2$ is a single covalent bond, —COO—, —OOC—, —$CH_2CH_2$—, —$CH_2O$— or —$OCH_2$— and the other of the groups $Y^1$ and $Y^2$ is a single covalent bond; and rings $A^1$ and $A^2$ each independently represent substituted or unsubstituted trans-1,4-cyclohexylene, in which optionally 2 non-adjacent $CH_2$ groups are replaced by oxygen, or substituted or unsubstituted 1,4-phenylene, in which optionally 1 CH group or 2 CH groups is/are replaced by nitrogen.

The term "substituted or unsubstituted trans-1,4-cyclohexylene, in which optionally 2 non-adjacent $CH_2$ groups are replaced by oxygen" embraces especially trans-1,4-cyclohexylene and trans-m-dioxane-2,5-diyl as well as rings which are substituted with substituents which are usual in liquid crystals, such as cyano, methyl, fluorine or chlorine, for example 1-cyano-trans-1,4-cyclohexylene or 2-methyl-trans-1,4-cyclohexylene.

The term "substituted or unsubstituted 1,4-phenylene, in which optionally 1 CH group or 2 CH groups is/are replaced by nitrogen" embraces especially 1,4-phenylene, pyridine-2,5-diyl, pyrazine-2,5-diyl and pyrimidine-2,5-diyl as well as rings which are substituted with substituents which are usual in liquid crystals, such as cyano, methyl, fluorine or chlorine, for example 2-cyano-1,4-phenylene, 2-fluoro-1,4-phenylene, 2-chloro-1,4-phenylene or 2-methyl-1,4-phenylene.

The cyano and halo compounds of formulas V, VI, VIII, IX, X, XII, XIV, XV, XIX, XXI and XXIII as well as the isothiocyanates of formula XXII are preferred mixture components having positive dielectric anisotropy. Preferably, the final mixture contains about 20-70 wt. %, especially about 25-50 wt. %, of one or more of these compounds.

The compounds of formulas VIII-XXI, especially the compounds of formulas XIII, XIV, XVI, XVII, XVIII, XIX and XX as well as the compounds of formula XXI in which rings $A^1$ and $A^2$ are trans-1,4-cyclohexylene, are preferred mixture components for the production of a low optical anisotropy in the final mixture.

Those mixtures which contain, in addition to one or more compounds of formula I, one or more compounds of formula VIII, X, XIV, XVI, XVII and/or XXI are generally especially preferred.

The mixtures in accordance with the invention can also contain optically active compounds (for example, optically active 4'-alkyl- or 4'-alkoxy-4-biphenylcarbonitriles) and/or dichroic coloring substances (for example, azo, azoxy or anthraquinone coloring substances). The amount of such compounds is determined by the solubility, the desired pitch, color, extinction and the like. In general, the amount of optically active compounds and dichroic coloring substances amounts to a maximum of in each case about 10 wt. % in the final mixture.

The manufacture of the mixtures in accordance with the invention and the manufacture of the electro-optical devices can be effected in a manner known per se.

The manufacture of the compounds of formula I and of liquid crystalline mixtures containing these compounds are illustrated in more detail by the following Examples. C is a crystalline phase, S is a smectic phase, $S_B$ is a smectic B phase, N is a nematic phase and I is the isotropic phase. $V_{10}$ denotes the voltage for 10% transmission (direction of view perpendicular to the plate surface). $t_{on}$ and $t_{off}$ denote the switching-on time and the switching-off time, respectively, and $\Delta n$ denotes the optical anisotropy.

The following Examples illustrate the present invention but are not intended to limit its extent in any manner.

Unless otherwise stated, percentages and ratios relating to solvent mixtures are expressed in volume, purity data determined by gas chromatography are expressed in area %, and the remaining percentages and ratios are expressed in weight. Temperatures are in degrees Celsius (°C.), normal pressure is about 1 atmosphere, and room temperature is about 23° C. Examples were carried out as written unless otherwise indicated.

EXAMPLE 1 a) A solution of 1.04 g of trans-4-[trans-4-(3-butenyl)-cyclohexyl]cyclohexanecarbonitrile in 10 ml of diethylene glycol was treated with a solution of 2 g of potassium hydroxide in 10 ml of diethylene glycol and then stirred at 180° C. (oil bath temperature) for 2.5 hours.

Subsequently, the reaction mixture was poured on to ice/water, acidified with 8 ml of 25 percent hydrochloric acid and extracted with diethyl ether. The organic phase was dried over magnesium sulphate, filtered and evaporated. Crystallization of the resulting beige crude product (1.06 g) from 50 ml of hexane gave 588 mg of trans-4-[trans-4-(3-butenyl)cyclohexyl]cyclohexanecarboxylic acid as colorless crystals.

b) A suspension of 1.55 g of lithium aluminium hydride in 30 ml of diethyl ether was treated dropwise at room temperature within 10 minutes with a solution of 2.7 g of trans-4-[trans-4-(3-butenyl)cyclohexyl]cyclohexanecarboxylic acid in 40 ml of diethyl ether. Subsequently, the reaction mixture was stirred under reflux (bath temperature 45° C.) for 1 hour, then treated at 0°-10° C. with 20 ml of 2N hydrochloric acid and extracted three times with diethyl ether. The organic phase was washed with 2N hydrochloric acid and twice with water, dried over magnesium sulphate, filtered and evaporated. There were thus obtained 2.5 g of [trans-4-[trans-4-(3-butenyl)cyclohexyl]cyclohexyl]methanol as colorless crystals.

The following compounds can be prepared in an analogous manner:

[trans-4-(trans-4-Methylcyclohexyl)cyclohexyl]methanol;
[trans-4-(trans-4-ethylcyclohexyl)cyclohexyl]methanol;
[trans-4-(trans-4-propylcyclohexyl)cyclohexyl]methanol;
[trans-4-(trans-4-butylcyclohexyl)cyclohexyl]methanol;
[trans-4-(trans-4-pentylcyclohexyl)cyclohexyl]methanol;
[trans-4-(trans-4-hexylcyclohexyl)cyclohexyl]methanol;
[trans-4-(trans-4-heptylcyclohexyl)cyclohexyl]methanol;
[trans-4-(trans-4-vinylcyclohexyl)cyclohexyl]methanol;
[trans-4-[trans-4-(1E-propenyl)cyclohexyl]cyclohexyl]methanol;
[trans-4-[trans-4-(1E-butenyl)cyclohexyl]cyclohexyl]methanol;
[trans-4-[trans-4-(1E-pentenyl)cyclohexyl]cyclohexyl]methanol;
[trans-4-[trans-4-(1E-hexenyl)cyclohexyl]cyclohexyl]methanol;
[trans-4-[trans-4-(1E-heptenyl)cyclohexyl]cyclohexyl]methanol;
[trans-4-[trans-4-(3E-pentenyl)cyclohexyl]cyclohexyl]methanol;
[trans-4-[trans-4-(3E-hexenyl)cyclohexyl]cyclohexyl]methanol;
[trans-4-[trans-4-(3E-heptenyl)cyclohexyl]cyclohexyl]methanol;
[trans-4-[trans-4-(4-pentenyl)cyclohexyl]cyclohexyl]methanol;
[trans-4-[trans-4-(4Z-hexenyl)cyclohexyl]cyclohexyl]methanol;
[trans-4-[trans-4-(4Z-heptenyl)cyclohexyl]cyclohexyl]methanol;
[trans-4-[2-(trans-4-methylcyclohexyl)ethyl]cyclohexyl]methanol;
[trans-4-[2-(trans-4-ethylcyclohexyl)ethyl]cyclohexyl]methanol;
[trans-4-[2-(trans-4-propylcyclohexyl)ethyl]cyclohexyl]methanol;
[trans-4-[2-(trans-4-butylcyclohexyl)ethyl]cyclohexyl]methanol;
[trans-4-[2-(trans-4-pentylcyclohexyl)ethyl]cyclohexyl]methanol;
[trans-4-[2-(trans-4-(1E-propenyl)cyclohexyl)ethyl]cyclohexyl]methanol;
[trans-4-[2-(trans-4-(1E-butenyl)cyclohexyl)ethyl]cyclohexyl]methanol;
[trans-4-[2-(trans-4-(1E-pentenyl)cyclohexyl)ethyl]cyclohexyl]methanol;
[trans-4-[2-(trans-4-(3-butenyl)cyclohexyl)ethyl]cyclohexyl]methanol;
[trans-4-[2-(trans-4-(3E-pentenyl)cyclohexyl)ethyl]cyclohexyl]methanol;
[trans-4-[2-(trans-4-(4-pentenyl)cyclohexyl)ethyl]cyclohexyl]methanol.

EXAMPLE 2 a) 780 mg of sodium borohydride were dissolved in 30 ml of methanol/diethyl ether (vol. 9:1). This solution was treated dropwise at 0° C. within 10 minutes with a solution of 6.0 g of trans-4-(trans-4-cyanocyclohexyl)-cyclohexanecarboxaldehyde in 40 ml of methanol/diethyl ether (vol. 9:1) and stirred further at 0° C. After 1.5 hours the reaction mixture was again treated with 200 ml of sodium borohydride and stirred at 0° C. for a further 3.5 hours. Subsequently, the reaction mixture was acidified (pH about 2) with 20 ml of dilute hydrochloric acid and extracted three times with methylene chloride. The organic phases were washed with dilute hydrochloric acid and twice with water, dried over magnesium sulphate and evaporated. The colorless, crystalline crude product (6.0 g) was purified by chromatography on silica gel with toluene/ethyl acetate (vol. 3:1) and crystallized from 120 ml of ethyl acetate/hexane (vol. 1:5). There were thus obtained 3.7 g of colorless, crystalline [trans-4-(trans-4-cyanocyclohexyl)cyclohexyl]methanol.

b) 1.2 g of sodium hydride (as a 50 percent suspension in oil) were suspended in 20 ml of tetrahydrofuran and treated dropwise at room temperature within 5 minutes with a solution of 3.7 g of [trans-4-(trans-4-cyanocyclohexyl)-cyclohexyl]methanol in 40 ml of tetrahydrofuran. The reaction mixture was stirred at room temperature for a further 5 minutes, then treated with 3.12 ml of methyl iodide and stirred under reflux (bath temperature 70° C.) for a further 2 hours. Subsequently, the white suspension was partitioned in diethyl ether/water and extracted three times with diethyl ether. The organic phases were washed twice with water, dried over magnesium sulphate, filtered and evaporated. The yellowish crude product (4.5 g) was purified by chromatography on silica gel with ethyl acetate/petroleum ether (vol. 5:95) and recrystallized several times from methanol. There were thus obtained 1.64 g of [trans-4-(trans-4-cyanocyclohexyl)cyclohexyl]-methyl methyl ether as colorless crystals]; m.p. (C-$S_B$) 23.4° C., phase transition ($S_B$-N) 62.0° C., cl.p. (N-I) 70° C.

The following compounds can be prepared in an analogous manner:

[trans-4-(trans-4-Cyanocyclohexyl)cyclohexyl]methyl ethyl ether;
[trans-4-(trans-4-cyanocyclohexyl)cyclohexyl]methyl propyl ether;
[trans-4-(trans-4-cyanocyclohexyl)cyclohexyl]methyl butyl ether;
[trans-4-(trans-4-cyanocyclohexyl)cyclohexyl]methyl pentyl ether;
[trans-4-(trans-4-cyanocyclohexyl)cyclohexyl]methyl allyl ether;

[trans-4-(trans-4-cyanocyclohexyl)cyclohexyl]methyl 2Z-butenyl ether;
[trans-4-(trans-4-cyanocyclohexyl)cyclohexyl]methyl 2Z-pentenyl ether;
[trans-4-[2-(trans-4-cyanocyclohexyl)ethyl]cyclohexyl]-methyl methyl ether;
[trans-4-[2-(trans-4-cyanocyclohexyl)ethyl]cyclohexyl]-methyl ethyl ether;
[trans-4-[2-(trans-4-cyanocyclohexyl)ethyl]cyclohexyl]-methyl propyl ether;
[trans-4-[2-(trans-4-cyanocyclohexyl)ethyl]cyclohexyl]-methyl butyl ether;
[trans-4-[2-(trans-4-cyanocyclohexyl)ethyl]cyclohexyl]-methyl pentyl ether;
[trans-4-[2-(trans-4-cyanocyclohexyl)ethyl]cyclohexyl]-methyl allyl ether;
[trans-4-[2-(trans-4-cyanocyclohexyl)ethyl]cyclohexyl]-methyl 2Z-butenyl ether;
[trans-4-[2-(trans-4-cyanocyclohexyl)ethyl]cyclohexyl]-methyl 2Z-pentenyl ether.

EXAMPLE 3 a) 1.5 g of [trans-4-(trans-4-cyanocyclohexyl)cyclohexyl]methyl methyl ether were suspended in 30 ml of glacial acetic acid and 15 ml of 50 percent sulphuric acid and the suspension was heated to reflux (bath temperature 130° C.) for 20 hours while stirring. Subsequently, the reaction mixture was partitioned in methylene chloride/water and extracted three times with methylene chloride. The organic phases were washed three times with water, dried over magnesium sulphate, filtered and evaporated. There were thus obtained 1.33 g of brown, oily trans-4-[trans-4-(methoxymethyl)cyclohexyl]cyclohexanecarboxylic acid which was used without purification.

b) A suspension of 390 mg of lithium aluminium hydride in 20 ml of diethyl ether was treated dropwise at room temperature within 5 minutes with a solution of 1.3 g of trans-4-[trans-4-(methoxymethyl)cyclohexyl]-cyclohexanecarboxylic acid in 40 ml of methylene chloride. The reaction mixture was stirred at 50° C. bath temperature for 1 hour, then treated with 100 mg of lithium aluminium hydride and stirred for a further 1 hour. Subsequently, the reaction mixture was treated dropwise at about 15° C. with 40 ml of water and extracted three times with methylene chloride. The organic phases were washed with dilute hydrochloric acid (pH about 1) and twice with water, dried over magnesium sulphate, filtered and evaporated. Chromatographic purification of the yellow crude product (0.96 g) on silica gel with toluene/ethyl acetate (vol. 5:1) gave yellowish, solid [trans-4-[trans-4-(methoxymethyl)cyclohexyl]cyclohexyl]methanol.

c) 150 mg of sodium hydride (as a 50 percent suspension in oil) is suspended in 10 ml of absolute tetrahydrofuran and then treated dropwise at room temperature within 3 minutes with a solution of 0.5 g of [trans-4-[trans-4-(methoxymethyl)cyclohexyl]cyclohexyl]methanol in 8 ml of absolute tetrahydrofuran. The mixture is stirred for a further 5 minutes, then treated with 0.755 g of allyl bromide and stirred under reflux (bath temperature 70° C.) for 16 hours. Thereafter, the reaction mixture is partitioned in diethyl ether/water and extracted three times with diethyl ether. The organic phases are washed twice with water, dried over magnesium sulphate, filtered and evaporated. Chromatographic purification of the resulting crude product on silica gel with ethyl acetate/petroleum ether (vol. 3:97) gives [trans-4-[trans-4-(methoxymethyl)cyclohexyl]cyclohexyl]-methyl allyl ether.

The following compounds can be prepared in an analogous manner:

[trans-4-[trans-4-(Methoxymethyl)cyclohexyl]cyclohexyl]methyl 2Z-butenyl ether;
[trans-4-]trans-4-(methoxymethyl)cyclohexyl]cyclohexyl]methyl 2Z-pentenyl ether;
[trans-4-[trans-4-(ethoxymethyl)cyclohexyl]cyclohexyl]-methyl allyl ether;
[trans-4-[trans-4-(ethoxymethyl)cyclohexyl]cyclohexyl]-methyl 2Z-butenyl ether;
[trans-4-[trans-4-(ethoxymethyl)cyclohexyl]cyclohexyl]-methyl 2Z-pentenyl ether;
[trans-4-[trans-4-(propyloxymethyl)cyclohexyl]cyclohexyl]methyl allyl ether;
[trans-4-[trans-4-(propyloxymethyl)cyclohexyl]cyclohexyl]methyl 2Z-butenyl ether;
[trans-4-[trans-4-(butyloxymethyl)cyclohexyl]cyclohexyl]methyl allyl ether;
[trans-4-[trans-4-(butyloxymethyl)cyclohexyl]cyclohexyl]methyl 2Z-butenyl ether;
[trans-4-[trans-4-(pentyloxymethyl)cyclohexyl]cyclohexyl]methyl allyl ether;
[trans-4-[trans-4-(allyloxymethyl)cyclohexyl]cyclohexyl]methyl allyl ether;
[trans-4-[trans-4-(allyloxymethyl)cyclohexyl]cyclohexyl]methyl 2Z-butenyl ether;
[trans-4-[trans-4-(allyloxymethyl)cyclohexyl]cyclohexyl]methyl 2Z-pentenyl ether;
[trans-4-[trans-4-(2Z-butenyloxymethyl)cyclohexyl]-cyclohexyl]methyl 2Z-butenyl ether;
[trans-4-[2-(trans-4-(methoxymethyl)cyclohexyl)ethyl]-cyclohexyl]methyl allyl ether;
[trans-4-[2-(trans-4-(methoxymethyl)cyclohexyl)ethyl]-cyclohexyl]methyl 2Z-butenyl ether;
[trans-4-[2-(trans-4-(ethoxymethyl)cyclohexyl)ethyl]-cyclohexyl]methyl allyl ether;
[trans-4-[2-(trans-4-(ethoxymethyl)cyclohexyl)ethyl]-cyclohexyl]methyl 2Z-butenyl ether;
[trans-4-[2-(trans-4-(propyloxymethyl)cyclohexyl)-ethyl]cyclohexyl]methyl allyl ether;
[trans-4-[2-(trans-4-(butyloxymethyl)cyclohexyl)ethyl]-cyclohexyl]methyl allyl ether;
[trans-4-[2-(trans-4-(pentyloxymethyl)cyclohexyl)-ethyl]cyclohexyl]methyl allyl ether;
[trans-4-[2-(trans-4-(allyloxymethyl)cyclohexyl)ethyl]-cyclohexyl]methyl allyl ether;
[trans-4-[2-(trans-4-(allyloxymethyl)cyclohexyl)ethyl]-cyclohexyl]methyl 2Z-butenyl ether;
[trans-4-[2-(trans-4-(2Z-butenyloxymethyl)cyclohexyl)-ethyl]cyclohexyl]methyl 2Z-butenyl ether.

EXAMPLE 4

290 mg of sodium hydride as a 50 percent suspension in oil were placed in a sulfonation flask and rinsed with 10 ml of pentane. The supernatant solution was then sucked off and the sodium hydride slurry was treated dropwise with a solution of 1.0 g of [trans-4-[trans-4-(3-butenyl)-cyclohexyl]cyclohexyl]methanol in 15 ml of tetrahydrofuran. The reaction mixture was stirred at room temperature, treated after 5 minutes with 0.745 ml of methyl iodide and stirred at 70° C. bath temperature for a further 3 hours. Subsequently, the reaction mixture was partitioned in diethyl ether/water and extracted three times with diethyl ether. The organic phases were washed twice with water, dried over magnesium sulphate, filtered and evaporated. The colorless crude product (1.1 g) was purified by chromatography on silica gel with ethyl acetate/petroleum ether (vol. 3:97) and crystallized from 40 ml at −20° C. There were thus obtained 727 mg of colorless, crystalline [trans-4-[trans-4-(3-butenyl)-cyclohexyl]cyclohexyl]methyl methyl ether: m.p. (C-S$_B$) −9.4° C., phase transition (S$_B$-N) 50.3° C., cl.p. (N-I) 53.0° C.

The following compounds can be prepared in an analogous manner:

[trans-4-(trans-4-Vinylcyclohexyl)cyclohexyl]methyl methyl ether, m.p. (C-S$_B$) 5.6° C., cl.p. (S$_B$-I) 17.1° C.;
[trans-4-[trans-4-(1E-propenyl)cyclohexyl]cyclohexyl]-methyl methyl ether, m.p. (C-S$_B$) 12.3° C., phase transition (S$_B$-N) 22.4° C., cl.p. (N-I) 62.2° C.;
[trans-4-[trans-4-(1E-butenyl)cyclohexyl]cyclohexyl]-methyl methyl ether, m.p. (C-S$_B$) 6.3° C., phase transition (S$_B$-N) 46.8° C., cl.p. (N-I) 49.0° C.;
[trans-4-[trans-4-(1E-pentenyl)cyclohexyl]cyclohexyl]-methyl methyl ether;
[trans-4-[trans-4-(1E-hexenyl)cyclohexyl]cyclohexyl]-methyl methyl ether;
[trans-4-[trans-4-(1E-heptenyl)cyclohexyl]cyclohexyl]-methyl methyl ether;
[trans-4-[trans-4-(3E-pentenyl)cyclohexyl]cyclohexyl]-methyl methyl ether, m.p. (C-N) 41° C., cl.p. (N-I) 74.3° C.;
[trans-4-[trans-4-(3E-hexenyl)cyclohexyl]cyclohexyl]-methyl methyl ether;
[trans-4-[trans-4-(3E-heptenyl)cyclohexyl]cyclohexyl]-methyl methyl ether;
[trans-4-[trans-4-(4-pentenyl)cyclohexyl]cyclohexyl]-methyl methyl ether, cl.p. 70.8° C.;
[trans-4-[trans-4-(4Z-hexenyl)cyclohexyl]cyclohexyl]-methyl methyl ether;
[trans-4-[trans-4-(4Z-heptenyl)cyclohexyl]cyclohexyl]-methyl methyl ether;
[trans-4-[trans-4-vinylcyclohexyl]cyclohexyl]methyl ethyl ether, m.p. (C-S$_B$) −19.6° C., cl.p. (S$_B$-I) 9.9° C.;
[trans-4-[trans-4-(1E-propenyl)cyclohexyl]cyclohexyl]-methyl ethyl ether, m.p. (C-N) 20.8° C., transition (S$_B$-N) 13.3° C., cl.p. (N-I) 34.1° C.;
[trans-4-[trans-4-(1E-butenyl)cyclohexyl]cyclohexyl]-methyl ethyl ether;
[trans-4-[trans-4-(1E-pentenyl)cyclohexyl]cyclohexyl]-methyl ethyl ether;
[trans-4-[trans-4-(1E-hexenyl)cyclohexyl]cyclohexyl]-methyl ethyl ether;
[trans-4-[trans-4-(1E-heptenyl)cyclohexyl]cyclohexyl]-methyl ethyl ether;
[trans-4-[trans-4-(3-butenyl)cyclohexyl]cyclohexyl]-methyl ethyl ether;
[trans-4-[trans-4-(3E-pentenyl)cyclohexyl]cyclohexyl]-methyl ethyl ether, m.p. (C-S$_B$) 14.3° C., cl.p. (S$_B$-I) 57.5° C.;
[trans-4-[trans-4-(3E-hexenyl)cyclohexyl]cyclohexyl]-methyl ethyl ether;
[trans-4-[trans-4-(3E-heptenyl)cyclohexyl]cyclohexyl]-methyl ethyl ether;
[trans-4-[trans-4-(4-pentenyl)cyclohexyl]cyclohexyl]-methyl ethyl ether;
[trans-4-[trans-4-(4Z-hexenyl)cyclohexyl]cyclohexyl]-methyl ethyl ether;
[trans-4-[trans-4-(4Z-heptenyl)cyclohexyl]cyclohexyl]-methyl ethyl ether;
[trans-4-[trans-4-vinylcyclohexyl]cyclohexyl]methyl propyl ether;
[trans-4-[trans-4-(1E-propenyl)cyclohexyl]cyclohexyl]-methyl propyl ether;
[trans-4-[trans-4-(1E-butenyl)cyclohexyl]cyclohexyl]-methyl propyl ether;
[trans-4-[trans-4-(1E-pentenyl)cyclohexyl]cyclohexyl]-methyl propyl ether;
[trans-4-[trans-4-(1E-hexenyl)cyclohexyl]cyclohexyl]-methyl propyl ether;
[trans-4-[trans-4-(1E-heptenyl)cyclohexyl]cyclohexyl]-methyl propyl ether;
[trans-4-[trans-4-(3-butenyl)cyclohexyl]cyclohexyl]-methyl propyl ether;
[trans-4-[trans-4-(3E-pentenyl)cyclohexyl]cyclohexyl]-methyl propyl ether;
[trans-4-[trans-4-(3E-hexenyl)cyclohexyl]cyclohexyl]-methyl propyl ether;
[trans-4-[trans-4-(3E-heptenyl)cyclohexyl]cyclohexyl]-methyl propyl ether;
[trans-4-[trans-4-(4-pentenyl)cyclohexyl]cyclohexyl]-methyl propyl ether;
[trans-4-[trans-4-(4Z-hexenyl)cyclohexyl]cyclohexyl]-methyl propyl ether;
[trans-4-[trans-4-(4Z-heptenyl)cyclohexyl]cyclohexyl]-methyl propyl ether;
[trans-4-(trans-4-methylcyclohexyl)cyclohexyl]methyl allyl ether;
[trans-4-(trans-4-ethylcyclohexyl)cyclohexyl]methyl allyl ether;
[trans-4-(trans-4-propylcyclohexyl)cyclohexyl]methyl allyl ether, cl.p. (S$_B$-I) 54° C.;
[trans-4-(trans-4-butylcyclohexyl)cyclohexyl]methyl allyl ether, m.p. (C-S$_B$) −1.4° C., cl.p. (S$_B$-I) 72.9° C.;
[trans-4-(trans-4-pentylcyclohexyl)cyclohexyl]methyl allyl ether;
[trans-4-(trans-4-hexylcyclohexyl)cyclohexyl]methyl allyl ether;
[trans-4-(trans-4-heptylcyclohexyl)cyclohexyl]methyl allyl ether;
[trans-4-[trans-4-vinylcyclohexyl]cyclohexyl]methyl allyl ether;
[trans-4-[trans-4-(1E-propenyl)cyclohexyl]cyclohexyl]-methyl allyl ether;
[trans-4-[trans-4-(1E-butenyl)cyclohexyl]cyclohexyl]-methyl allyl ether;
[trans-4-[trans-4-(1E-pentenyl)cyclohexyl]cyclohexyl]-methyl allyl ether;
[trans-4-[trans-4-(1E-hexenyl)cyclohexyl]cyclohexyl]-methyl allyl ether;
[trans-4-[trans-4-(1E-heptenyl)cyclohexyl]cyclohexyl]-methyl allyl ether;
[trans-4-[trans-4-(3-butenyl)cyclohexyl]cyclohexyl]-methyl allyl ether;
[trans-4-[trans-4-(3E-pentenyl)cyclohexyl]cyclohexyl]-methyl allyl ether;
[trans-4-[trans-4-(3E-hexenyl)cyclohexyl]cyclohexyl]-methyl allyl ether;
[trans-4-[trans-4-(3E-heptenyl)cyclohexyl]cyclohexyl]-methyl allyl ether;
[trans-4-[trans-4-(4-pentenyl)cyclohexyl]cyclohexyl]-methyl allyl ether;
[trans-4-[trans-4-(4Z-hexenyl)cyclohexyl]cyclohexyl]-methyl allyl ether;
[trans-4-[trans-4-(4Z-heptenyl)cyclohexyl]cyclohexyl]-methyl allyl ether;
[trans-4-(trans-4-methylcyclohexyl)cyclohexyl]methyl 2Z-butenyl ether;
[trans-4-(trans-4-ethylcyclohexyl)cyclohexyl]methyl 2Z-butenyl ether;

[trans-4-(trans-4-propylcyclohexyl)cyclohexyl]methyl 2Z-butenyl ether;
[trans-4-(trans-4-butylcyclohexyl)cyclohexyl]methyl 2Z-butenyl ether;
[trans-4-(trans-4-pentylcyclohexyl)cyclohexyl]methyl 2Z-butenyl ether;
[trans-4-(trans-4-hexylcyclohexyl)cyclohexyl]methyl 2Z-butenyl ether;
[trans-4-(trans-4-heptylcyclohexyl)cyclohexyl]methyl 2Z-butenyl ether;
[trans-4-[trans-4-vinylcyclohexyl]cyclohexyl]methyl 2Z-butenyl ether;
[trans-4-[trans-4-(1E-propenyl)cyclohexyl]cyclohexyl]methyl 2Z-butenyl ether;
[trans-4-[trans-4-(1E-butenyl)cyclohexyl]cyclohexyl]methyl 2Z-butenyl ether;
[trans-4-[trans-4-(1E-pentenyl)cyclohexyl]cyclohexyl]methyl 2Z-butenyl ether;
[trans-4-[trans-4-(1E-hexenyl)cyclohexyl]cyclohexyl]methyl 2Z-butenyl ether;
[trans-4-[trans-4-(1E-heptenyl)cyclohexyl]cyclohexyl]methyl 2Z-butenyl ether;
[trans-4-[trans-4-(3-butenyl)cyclohexyl]cyclohexyl]methyl 2Z-butenyl ether;
[trans-4-[trans-4-(3E-pentenyl)cyclohexyl]cyclohexyl]methyl 2Z-butenyl ether;
[trans-4-[trans-4-(3E-hexenyl)cyclohexyl]cyclohexyl]methyl 2Z-butenyl ether;
[trans-4-[trans-4-(3E-heptenyl)cyclohexyl]cyclohexyl]methyl 2Z-butenyl ether;
[trans-4-[trans-4-(4-pentenyl)cyclohexyl]cyclohexyl]methyl 2Z-butenyl ether;
[trans-4-[trans-4-(4Z-hexenyl)cyclohexyl]cyclohexyl]methyl 2Z-butenyl ether;
[trans-4-[trans-4-(4Z-heptenyl)cyclohexyl]cyclohexyl]methyl 2Z-butenyl ether;
[trans-4-[2-(trans-4-methylcyclohexyl)ethyl]cyclohexyl]methyl methyl ether;
[trans-4-[2-(trans-4-ethylcyclohexyl)ethyl]cyclohexyl]methyl methyl ether;
[trans-4-[2-(trans-4-propylcyclohexyl)ethyl]cyclohexyl]methyl methyl ether, m.p. (C-S$_B$) 29.7° C., cl.p. (S$_B$-I) 58.3° C.;
[trans-4-[2-(trans-4-butylcyclohexyl)ethyl]cyclohexyl]methyl methyl ether, m.p. (C-S$_B$) −1.2° C., cl.p. (S$_B$-I) 73.3° C.;
[trans-4-[2-(trans-4-pentylcyclohexyl)ethyl]cyclohexyl]methyl methyl ether, m.p. (C-S$_B$) 3.9° C., cl.p. (S$_B$-I) 81.0° C.;
[trans-4-[2-(trans-4-hexylcyclohexyl)ethyl]cyclohexyl]methyl methyl ether;
[trans-4-[2-(trans-4-heptylcyclohexyl)ethyl]cyclohexyl]methyl methyl ether;
[trans-4-[2-(trans-4-methylcyclohexyl)ethyl]cyclohexyl]methyl ethyl ether;
[trans-4-[2-(trans-4-ethylcyclohexyl)ethyl]cyclohexyl]methyl ethyl ether;
[trans-4-[2-(trans-4-propylcyclohexyl)ethyl]cyclohexyl]methyl ethyl ether;
[trans-4-[2-(trans-4-butylcyclohexyl)ethyl]cyclohexyl]methyl-ethyl ether;
[trans-4-[2-(trans-4-pentylcyclohexyl)ethyl]cyclohexyl]methyl ethyl ether;
[trans-4-[2-(trans-4-methylcyclohexyl)ethyl]cyclohexyl]methyl propyl ether;
[trans-4-[2-(trans-4-ethylcyclohexyl)ethyl]cyclohexyl]methyl propyl ether;
[trans-4-[2-(trans-4-propylcyclohexyl)ethyl]cyclohexyl]methyl propyl ether;
[trans-4-[2-(trans-4-butylcyclohexyl)ethyl]cyclohexyl]methyl propyl ether;
[trans-4-[2-(trans-4-(methoxymethyl)cyclohexyl)ethyl]cyclohexyl]methyl methyl ether;
[trans-4-[2-(trans-4-(methoxymethyl)cyclohexyl)ethyl]cyclohexyl]methyl ethyl ether;
[trans-4-[2-(trans-4-(ethoxymethyl)cyclohexyl)ethyl]cyclohexyl]methyl ethyl ether;
[trans-4-[2-(trans-4-(methoxymethyl)cyclohexyl)ethyl]cyclohexyl]methyl propyl ether;
[trans-4-[2-(trans-4-(ethoxymethyl)cyclohexyl)ethyl]cyclohexyl]methyl propyl ether;
[trans-4-[2-(trans-4-(propyloxymethyl)cyclohexyl)ethyl]cyclohexyl]methyl propyl ether;
[trans-4-[2-(trans-4-(methoxymethyl)cyclohexyl)ethyl]cyclohexyl]methyl butyl ether;
[trans-4-[2-(trans-4-(ethoxymethyl)cyclohexyl)ethyl]cyclohexyl]methyl butyl ether;
[trans-4-[2-(trans-4-vinylcyclohexyl)ethyl]cyclohexyl]methyl methyl ether;
[trans-4-[2-(trans-4-(1E-propenyl)cyclohexyl)ethyl]cyclohexyl]methyl methyl ether;
[trans-4-[2-(trans-4-(1E-butenyl)cyclohexyl)ethyl]cyclohexyl]methyl methyl ether;
[trans-4-[2-(trans-4-(1E-pentenyl)cyclohexyl)ethyl]cyclohexyl]methyl methyl ether;
[trans-4-[2-(trans-4-(3-butenyl)cyclohexyl)ethyl]cyclohexyl]methyl methyl ether;
[trans-4-[2-(trans-4-(3E-pentenyl)cyclohexyl)ethyl]cyclohexyl]methyl methyl ether;
[trans-4-[2-(trans-4-(4-pentenyl)cyclohexyl)ethyl]cyclohexyl]methyl methyl ether;
[trans-4-[2-(trans-4-vinylcyclohexyl)ethyl]cyclohexyl]methyl ethyl ether;
[trans-4-[2-(trans-4-(1E-propenyl)cyclohexyl)ethyl]cyclohexyl]methyl ethyl ether;
[trans-4-[2-(trans-4-(1E-butenyl)cyclohexyl)ethyl]cyclohexyl]methyl ethyl ether;
[trans-4-[2-(trans-4-(1E-pentenyl)cyclohexyl)ethyl]cyclohexyl]methyl ethyl ether;
[trans-4-[2-(trans-4-(3-butenyl)cyclohexyl)ethyl]cyclohexyl]methyl ethyl ether;
[trans-4-[2-(trans-4-(3E-pentenyl)cyclohexyl)ethyl]cyclohexyl]methyl ethyl ether;
[trans-4-[2-(trans-4-(4-pentenyl)cyclohexyl)ethyl]cyclohexyl]methyl ethyl ether;
[trans-4-[2-(trans-4-methylcyclohexyl)ethyl]cyclohexyl]methyl allyl ether;
[trans-4-[2-(trans-4-ethylcyclohexyl)ethyl]cyclohexyl]methyl allyl ether;
[trans-4-[2-(trans-4-propylcyclohexyl)ethyl]cyclohexyl]methyl allyl ether, m.p. (C-S$_B$) −6.5° C., cl.p. (S$_B$-I) 62.4° C.;
[trans-4-[2-(trans-4-butylcyclohexyl)ethyl]cyclohexyl]methyl allyl ether, m.p. (C-S$_B$) −4.1° C., cl.p. (S$_B$-I) 76.5° C.;
[trans-4-[2-(trans-4-pentylcyclohexyl)ethyl]cyclohexyl]methyl allyl ether, m.p. (C-S$_B$) −15.9° C., cl.p. (S$_B$-I) 83.6° C.;
[trans-4-[2(trans-4-vinylcyclohexyl)ethyl]cyclohexyl]methyl allyl ether;
[trans-4-[2-(trans-4-(1E-propenyl)cyclohexyl)ethyl]cyclohexyl]methyl allyl ether;
[trans-4-[2-(trans-4-(1E-butenyl)cyclohexyl)ethyl]cyclohexyl]methyl allyl ether;

[trans-4-[2-(trans-4-(1E-pentenyl)cyclohexyl)ethyl]-cyclohexyl]methyl allyl ether;
[trans-4-[2-(trans-4-(3-butenyl)cyclohexyl)ethyl]cyclohexyl]methyl allyl ether;
[trans-4-[2-(trans-4-(3E-pentenyl)cyclohexyl)ethyl]cyclohexyl]methyl allyl ether;
[trans-4-[2-(trans-4-(4-pentenyl)cyclohexyl)ethyl]cyclkohexyl]methyl allyl ether;
[trans-4-[trans-4-(methoxymethyl)cyclohexyl]cyclohexyl]methyl allyl ether;
[trans-4-[trans-4-(methoxymethyl)cyclohexyl]cyclohexyl]methyl 2Z-butenyl ether;
[trans-4-[trans-4-(methoxymethyl)cyclohexyl]cyclohexyl]methyl 2Z-pentenyl ether;
[trans-4-[trans-4-(ethoxymethyl)cyclohexyl]cyclohexyl]-methyl allyl ether;
[trans-4-[trans-4-(ethoxymethyl)cyclohexyl]cyclohexyl]-methyl 2Z-butenyl ether;
[trans-4-[trans-4(ethoxymethyl)cyclohexyl]cyclohexyl]-methyl 2Z-pentenyl ether;
[trans-4-[trans-4-(propyloxymethyl)cyclohexyl]cyclohexyl]-methyl allyl ether;
[trans-4-[trans-4-(propyloxymethyl)cyclohexyl]cyclohexyl]methyl 2Z-butenyl ether;
[trans-4-[trans-4-(butyloxymethyl)cyclohexyl]cyclohexyl]methyl allyl ether;
[trans-4-[trans-4-(butyloxymethyl)cyclohexyl]cyclohexyl]methyl 2Z-butenyl ether;
[trans-4-[trans-4-(pentyloxymethyl)cyclohexyl]cyclohexyl]methyl allyl ether;
[trans-4-[trans-4-(allyloxymethyl)cyclohexyl]cyclohexyl]methyl allyl ether;
[trans-4-[trans-4-(allyloxymethyl)cyclohexyl]cyclohexyl]methyl 2Z-butenyl ether;
[trans-4-[trans-4-(allyloxymethyl)cyclohexyl]cyclohexyl]methyl 2Z-pentenyl ether;
[trans-4-[trans-4-(2Z-butenyloxymethyl)cyclohexyl]-cyclohexyl]methyl 2Z-butenyl ether;
[trans-4-[2-(trans-4-(methoxymethyl)cyclohexyl)ethyl]-cyclohexyl]methyl allyl ether;
[trans-4-[2-(trans-4-(methoxymethyl)cyclohexyl)ethyl]-cyclohexyl]methyl 2Z-butenyl ether;
[trans-4-[2-(trans-4-(ethoxymethyl)cyclohexyl)ethyl]-cyclohexyl]methyl allyl ether;
[trans-4-[2-(trans-4-(ethoxymethyl)cyclohexyl)ethyl]-cyclohexyl]methyl 2Z-butenyl ether;
[trans-4-[2-(trans-4-(propyloxymethyl)cyclohexyl)-ethyl]cyclohexyl]methyl allyl ether;
[trans-4-[2-(trans-4-(butyloxymethyl)cyclohexyl)ethyl]-cyclohexyl]methyl allyl ether;
[trans-4-[2-(trans-4-(pentyloxymethyl)cyclohexyl)-ethyl]cyclohexyl]methyl allyl ether;
[trans-4-[2-(trans-4-(allyloxymethyl)cyclohexyl)ethyl]-cyclohexyl]methyl allyl ether;
[trans-4-[2-(trans-4-(allyloxymethyl)cyclohexyl)ethyl]-cyclohexyl]methyl 2Z-butenyl ether;
[trans-4-[2-(trans-4-(2Z-butenyloxymethyl)cyclohexyl)-ethyl]cyclohexyl]methyl 2Z-butenyl ether.

EXAMPLE 5

In order to investigate the influence of the compounds in accordance with the invention on the electro-optical properties of liquid crystalline mixtures, the following binary mixtures (BM) with 4-(trans-4-pentylcyclohexyl)-benzonitrile were prepared and compared with corresponding mixtures of alkoxy- or alkenyloxycylohexanes. The electro-optical data were measured at 22° C. in a TN cell having a plate separation of 8 μm; the response times were determined at the 2.5-fold value of $V_{10}$. The corresponding values for pure 4-(trans-4-pentylcyclohexyl)benzonitrile are: cl.p. (N-I) 54.6° C., $V_{10}$=1.62 V, $t_{on}$=30 ms, $t_{off}$=42 ms, $\Delta n$=0.120.

BM-1

50 wt. % of [trans-4-[trans-4-(3-butenyl)cyclohexyl]cyclohexyl]methyl methyl ether,
50 wt. % of 4-(trans-4-pentylcyclohexyl)benzonitrile;
cl.p. (N-I) 52.6° C., $V_{10}$=1.73 V, $t_{on}$=14 ms, $t_{off}$=29 ms, $\Delta n$=0.085.

BM-2

50 wt. % of [trans-4-(trans-4-vinylcyclohexyl)cyclohexyl]methyl methyl ether,
50 wt. % of 4-(trans-4-pentylcyclohexyl)benzonitrile;
cl.p. (N-I) 38.3° C., $V_{10}$=1.41 V, $t_{on}$=14 ms, $t_{off}$=29 ms, $\Delta n$=0.067.

BM-3

50 wt. % of [trans-4-[trans-4-(1E-propenyl)cyclohexyl]cyclohexyl]methyl methyl ether,
50 wt. % of 4-(trans-4-pentylcyclohexyl)benzonitrile;
cl.p. (N-I) 55.9° C., $V_{10}$=1.87 V, $t_{on}$=13 ms, $t_{off}$=25 ms, $\Delta n$=0.092.

BM-4

50 wt. % of [trans-4-[trans-4-(4-pentenyl)cyclohexyl]cyclohexyl]methyl methyl ether,
50 wt. % of 4-(trans-4-pentylcyclohexyl)benzonitrile;
cl.p. (N-I) 42.4° C., $V_{10}$=1.41 V, $t_{on}$=20 ms, $t_{off}$=45 ms, $\Delta n$=0.074.

COMPARATIVE MIXTURE 1

50 wt. % of trans-4-allyloxy-1-(trans-4-ethylcyclohexyl)-cyclohexane,
50 wt. % of 4-(trans-4-pentylcyclohexyl)benzonitrile;
cl.p (N-I) 49.9° C., $V_{10}$=1.38 V, $t_{on}$=26 ms, $t_{off}$=42 ms, $\Delta n$=0.114.

COMPARATIVE MIXTURE 2

50 wt. % of trans-4-ethoxy-1-[trans-4-(3-butenyl)cyclohexyl)cyclohexane.
50 wt. % of 4-(trans-4-pentylcyclohexyl)benzonitrile;
cl.p. (N-I) 44.4° C., $V_{10}$=1.66 V, $t_{on}$=21 ms, $t_{off}$=31 ms, $\Delta n$=0.082.

EXAMPLE 6

The nematic mixtures of the compositions given in Tables 1 and 3 illustrate the use of the compounds in accordance with the invention in complex liquid crystal mixtures. The concentration data in Tables 1 and 3 are given in weight percent. The physcial data of the mixtures are given in Tables 2 and 4. The electro-optical data were measured at 22° C. in a TN cell having a plate separation of 6 μm (for mixtures M-1 to M-4 in Table 2) and 8 μm (for mixtures M-5 to M-8 in Table 4), with theresponse times being determined at a voltage corresponding to the 2.5-fold value of $V_{10}$. M-8 is a comparative mixture to M-7 without the compound of formula I. The abbrevations used for the components in Tables 1 and 3 have the following significances:

2P(1)P2 = 5-ethyl-2-(4-ethylphenyl) pyrimidine,
0(3)P(1)P2 = 5-(3-butenyl)-2-(4-ethylphenyl)pyrimidine,
0(4)P(1)P2 = 5-(4-pentenyl)-2-(4-ethylphenyl)pyrimidine, 0(3)P(1)PF = 5-(3-butenyl)-2-(4-fluorophenyl)pyrimidine, 3CP02 = 4-ethoxy-1-(trans-4-propylcyclohexyl)benzene, 3CP = 4-(trans-4-propylcyclohexy)benzonitrile, 0d(1)CP = 4-(trans-4-vinylcyclohexyl)benzonitrile, 1d(1)CP = 4-[trans-4-(1E-propenyl)cyclohexyl]benzonitrile, 2d(1)CP = 4-[trans-4-(1E-butenyl)cyclohexyl]benzonitrile, 0(3)CP = 4-[trans-4-(3-butenyl)cyclohexyl]benzonitrile, 3CPS = 4-(trans-4-propylcyclohexyl)phenylisothiocyanate, 1d(3)CCO1 = trans-4-methoxy-1-[trans-4-(3E-pentenyl)cyclohexyl]cyclohexane, 0d(3)CCO2 = trans-4-ethoxy-1-[trans-4-(3-butenyl)cyclohexyl]cyclohexane, 1d(3)CCO2 = trans-4-ethoxy-1-4-(3E-pentenyl)cyclohexyl]cyclohexane, 0d(4)CCO2 = trans-4-ethoxy-1-[trans-4-(4-pentenyl)cyclohexyl]cyclohexane, 3CAPO2 = 4-ethoxy-1-[2(trans-4-propylcyclohexyl)ethyl]-benzene, 2CP(1)P5 = 5-(trans-4-ethylcyclohexyl)-2-(4-pentylphenyl)-pyrimidine, 1d(3)CPP2 = 4'-ethyl-4-[trans-4-(3E-pentenyl)cyclohexyl]-biphenyl, 1d(3)CPP3 = 4'-[trans-4-(3E-pentenyl)cyclohexyl]-biphenyl, 1d(1)CCP1 = 4-methyl-1-[trans-4-(trans-4-(1E-propenyl)-cyclohexyl)cyclohexyl]benzene, 3CCPF = 4-fluoro-1-[trans-4-propylcyclohexyl)-cyclohexyl]benzene, 0d(1)CCPF = 4-fluoro-1-[trans-4-(trans-4-vinylcyclohexyl)-cyclohexyl]benzene, 1d(1)CCPF = 4-fluoro-1-[trans-4-(trans-4-(1E-propenyl)cyclohexyl)cyclohexyl]benzene, 0d(3)CCPF = 4-fluoro-1-[trans-4-(trans-4-(3-butenyl)cyclohexyl)cyclohexyl]benzene, 3d(1) CPC3 = 4-(trans-4-propylcyclohexyl)-1-[trans-4-(1E-pentenyl)cyclohexyl]benzene, 5CPAC4 = 4-(trans-5-pentylcyclohexyl)-1-[2-(trans-4-butylcyclohexyl)ethyl]benzene, 0d(3)CCEPF = trans-4-[trans-4-(3-butenyl)cyclohexyl]-cyclohexanecarboxylic acid 4-fluorophenyl ester, 3CEPCd(3)1 = trans-4-propylcyclohexanecarboxylic acid 4-[trans-4-(3E-pentenyl)cyclohexyl]phenyl ester, 3CPPC3 = 4,4'-bis(trans-4-propylcyclohexyl)biphenyl, 5CP(1)PC3 = 5-(trans-4-pentylcyclohexyl)-2-[4-(trans-4-propylcyclohexyl)phenyl]pyrimidine, 5CPPAC4 = 4'-(trans-4-pentylcyclohexyl)-4-[2-(trans-4-butylcyclohexyl)ethyl]biphenyl, 0d(1)CC1O1 = [trans-4-(trans-4-vinylcyclohexyl)cyclohexyl]-methyl methyl ether, 1d(1)CC1O1 = [trans-4-[trans-4-(1E-propenyl)cyclohexyl]-cyclohexyl]methyl methyl ether, 0d(3)CC1O1 = [trans-4-[trans-4-(3-butenyl)cyclohexyl]cyclohexyl]methyl methyl ether, 3CC1Od(4)0 = [trans-4(trans-4-propylcyclohexyl)cyclohexyl]methyl allyl ether.

TABLE 1

| Mixture | Concentration data in wt. % | | | |
|---|---|---|---|---|
| | M-1 | M-2 | M-3 | M-4 |
| 3CP02 | 6% | 6% | 6% | — |
| 3CP | 10% | 10% | 10% | 10% |
| 0d(1)CP | 7% | 7% | 7% | 7% |
| 1d(1)CP | 8% | 8% | 8% | 8% |
| 1d(3)CC01 | 10% | 10% | 10% | 10% |
| 0d(3)CC02 | 10% | 10% | 10% | 10% |
| 0d(4)CC02 | — | — | — | 6% |
| 1d(1)CCP1 | — | — | — | 6% |
| 3CCPF | 8% | 8% | 8% | — |
| 0d(1)CCPF | — | — | — | 5% |
| 1d(1)CCPF | — | — | — | 5% |
| 3d(1)CPC3 | 8% | 8% | 8% | — |
| 5CPAC4 | 8% | 8% | 8% | 8% |
| 3CEPCd(3)1 | 6% | 6% | 6% | 6% |
| 3CPPC3 | 4% | 4% | 4% | — |
| 5CP(1)PC3 | 3% | 3% | 3% | 3% |
| 5CPPAC4 | — | — | — | 4% |
| 0d(1)CC101 | 12% | — | — | — |
| 1d(1)CC101 | — | — | — | 12% |
| 0d(3)CC101 | — | — | 12% | — |
| 3CC10d(4)0 | — | 12% | — | — |

TABLE 2

| Mixture | M-1 | M-2 | M-3 | M-4 |
|---|---|---|---|---|
| $V_{10}$ | 2.15 V | 2.20 V | 2.28 V | 2.30 V |
| $t_{on}$ | | | | |
| (22° C.) | 11 ms | 13 ms | 11 ms | 11 ms |
| (−20° C.) | 157 ms | 174 ms | 165 ms | 178 ms |
| (−30° C.) | 416 ms | 425 ms | 450 ms | 497 ms |
| $t_{off}$ | | | | |
| (22° C.) | 22 ms | 23 ms | 20 ms | 20 ms |
| (−20° C.) | 229 ms | 253 ms | 244 ms | 256 ms |
| (−30° C.) | 565 ms | 609 ms | 596 ms | 657 ms |
| M.p. | <−40° C. | <−40° C. | <−40° C. | <−30° C. |
| Cl.p. (N-I) | 85° C. | 85° C. | 89° C. | 93° C. |
| Δn | 0.098 | 0.095 | 0.099 | 0.090 |

TABLE 3

| Mixture | Concentration data in wt. % | | | |
|---|---|---|---|---|
| | M-5 | M-6 | M-7 | M-8 |
| 2P(1)P2 | | 8% | 8.00% | 8.00% |
| 0d(3)P(1)P2 | 6% | | | |
| 0d(4)P(1)P2 | 5% | | | |
| 0d(3)P(1)PF | 5% | | | |
| 3CP | 7% | 6% | 5.88% | 6.44% |
| 1d(1)CP | 6% | 10% | 9.24% | 10.12% |
| 2d(1)CP | 9% | | | |
| 0d(3)CP | | 7% | 6.72% | 7.36% |
| 3CPS | 8% | 9% | 7.56% | 8.28% |
| 1d(3)CC02 | | | 8.40% | 9.20% |
| 3CAP02 | | 7% | 8.40% | 9.20% |
| 2CP(1)P5 | 4% | | | |
| 1d(3)CPP2 | 5% | 5% | 4.20% | 4.60% |
| 1d(3)CPP3 | 6% | 6% | 5.04% | 5.52% |
| 1d(1)CCP1 | 6% | | | |
| 1d(1)CCPF | 5% | 4% | 3.36% | 3.68% |
| 0d(3)CCPF | 5% | | | |
| 0d(3)CCEPF | 6% | 8% | 6.72% | 7.36% |
| 3CEPCd(3)1 | 5% | 4% | 4.20% | 4.60% |
| 5CPAC4 | | 8% | 7.56% | 8.28% |
| 5CP(1)PC3 | 2% | 3% | 2.52% | 2.76% |
| 5CPPAC4 | | 5% | 4.20% | 4.60% |
| 1d(1)CC101 | 10% | 10% | 8.00% | |

TABLE 4

| Mixture | M-5 | M-6 | M-7 | M-8 |
|---|---|---|---|---|
| $V_{10}$ | 2.18 V | 2.42 V | 2.43 V | 2.4 V |
| $t_{on}$ | | | | |
| (22° C.) | 16 ms | 19 ms | 17 ms | 18 ms |
| (−20° C.) | 287 ms | 322 ms | 281 ms | 301 ms |
| (−30° C.) | 888 ms | 984 ms | 830 ms | 931 ms |
| $t_{off}$ | | | | |
| (22° C.) | 29 ms | 32 ms | 30 ms | 31 ms |
| (−20° C.) | 419 ms | 477 ms | 397 ms | 424 ms |
| (−30° C.) | 1270 ms | 1441 ms | 1120 ms | 1275 ms |

TABLE 4-continued

| Mixture | M-5 | M-6 | M-7 | M-8 |
|---|---|---|---|---|
| M.p. | <−30° C. | <−30° C. | <−30° C. | <−30° C. |
| Cl.p. (N-I) | 91° C. | 96° C. | 89° C. | 93° C. |
| Δn | 0.139 | 0.135 | 0.127 | 0.133 |

We claim:

1. A compound of formula $$R^1-O-CH_2-\langle\text{cyclohexyl}\rangle-Z-\langle\text{cyclohexyl}\rangle-R^2 \qquad I$$

wherein Z is a single covalent bond or —CH$_2$—CH$_2$—; $R^1$ is alkyl of 1 to 10 carbon atoms or 2-alkenyl of 3 to 10 carbon atoms; and $R^2$ is 1E-alkenyl, 3E-alkenyl, 4-alkenyl, (2-alkenyl)oxymethyl, alkyl, or alkoxymethyl having from 1 to 12 carbon atoms; with the proviso that $R^1$ is 2-alkenyl and Z is —CH$_2$CH$_2$— when $R^2$ is alkyl or alkoxymethyl.

2. A compound according to claim 1, wherein $R^1$ and $R^2$ each are straight-chain residues.

3. A compound according to claim 1, wherein $R^1$ has a maximum of 10 carbon atoms.

4. A compound according to claim 3, wherein $R^1$ has a maximum of 5 carbon atoms.

5. A compound according to claim 1, wherein $R^2$ has a maximum of 12 carbon atoms.

6. A compound according to claim 5, wherein $R^2$ has a maximum of 7 carbon atoms.

7. A compound according to claim 1, wherein $R^1$ is 2-alkenyl.

8. A compound according to claim 7, wherein $R^2$ is 1E-alkenyl, 3E-alkenyl, 4-alkenyl or (2-alkenyl)oxymethyl.

9. A compound according to claim 1, wherein $R^2$ is 1E-alkenyl, 3E-alkenyl, 4-alkenyl or (2-alkenyl)oxymethyl.

10. A liquid crystalline mixture having at least two components, wherein at least one component is a compound of formula $$R^1-O-CH_2-\langle\text{cyclohexyl}\rangle-Z-\langle\text{cyclohexyl}\rangle-R^2 \qquad I$$

wherein Z is a single covalent bond or —CH$_2$—CH$_2$—; $R^1$ is alkyl of 1 to 10 carbon atoms or 2-alkenyl of 3 to 10 carbon atoms; and $R^2$ is 1E-alkenyl, 3E-alkenyl, 4-alkenyl, (2-alkenyl)oxymethyl, alkyl or alkoxymethyl having from 1 to 12 carbon atoms; with the proviso that $R^1$ is 2-alkenyl and Z is —CH$_2$CH$_2$— when $R^2$ is alkyl or alkoxymethyl.

11. A liquid crystalline mixture according to claim 10, comprising one or more of the compounds of formula I; and one or more compounds having a positive dielectric anisotropy.

12. A liquid crystalline mixture according to claim 11, comprising one or more of the compounds of formula I; and one or more compounds from a group of compounds of formula V   $R^3$—⟨phenyl⟩—⟨phenyl⟩—CN VI  $R^3$—⟨pyrimidinyl⟩—⟨phenyl⟩—$R^4$ VII $R^5$—⟨phenyl⟩—C≡C—⟨phenyl⟩—$R^6$ VIII $R^7$—⟨cyclohexyl⟩—⟨pyrimidinyl⟩—CN IX  $R^7$—⟨dioxanyl⟩—⟨phenyl⟩—CN X   $R^7$—⟨cyclohexyl⟩—⟨phenyl⟩—$R^8$ XI  $R^7$—⟨cyclohexyl⟩—COO—⟨phenyl⟩—$R^9$ XII $R^7$—⟨cyclohexyl⟩—CH$_2$CH$_2$—⟨phenyl⟩$_n$—$R^8$ XIII $R^7$—⟨cyclohexyl⟩—Z—⟨cyclohexyl(CN)(R$^3$)⟩

XIV $R^7$—⟨cyclohexyl⟩—Z—⟨cyclohexyl⟩—$R^8$

XV  $R^7$—⟨cyclohexyl⟩—⟨phenyl⟩—⟨phenyl⟩—$R^8$

XVI $R^7$—⟨cyclohexyl⟩—⟨cyclohexyl⟩—⟨phenyl⟩—$R^8$

-continued

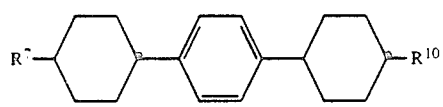 XVII
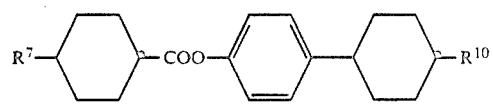 XVIII

 XIX

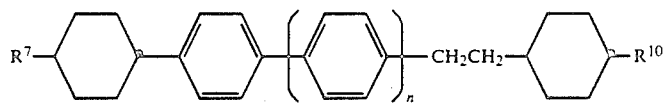 XX

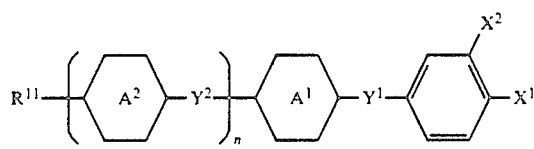 XXI

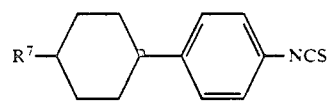 XXII
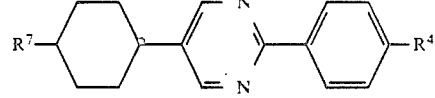 XXIII

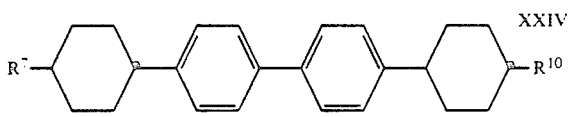 XXIV
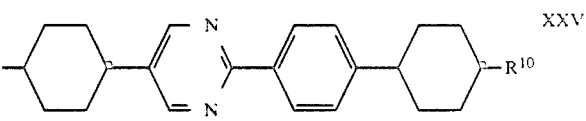 XXV wherein $R^3$ is alkyl, 3E-alkenyl or 4-alkenyl; $R^4$ is alkyl, cyano or fluorine; $R^5$ and $R^6$ each independently are alkyl or alkoxy; $R^7$ and $R^{10}$ each independently are alkyl, 1E-alkenyl, 3E-alkenyl or 4-alkenyl; $R^8$ is cyano, alkyl, 1E-alkenyl, 3E-alkenyl, 4-alkenyl, alkoxy, 2E-alkenyloxy or 3-alkenyloxy; $R^9$ is alkoxy, 2E-alkenyloxy or 3-alkenyloxy; n stands for the number 0 or 1; Z is a single covalent bond or —CH$_2$CH$_2$—; $X^1$ is fluorine or chlorine; and $X^2$ is hydrogen, fluorine or chlorine; $R^{11}$ is alkyl, 3E-alkenyl, 4-alkenyl, alkoxy, 2E-alkenyloxy or 3-alkenyloxy; one of the groups $Y^1$ and $Y^2$ is a single covalent bond, —COO—, —OOC—, —CH$_2$CH$_2$—, —CH$_2$O— or —OCH$_2$— and the other of the groups $Y^1$ and $Y^2$ is a single covalent bond; and rings $A^1$ and $A^2$ each independently are unsubstituted trans-1,4-cyclohexylene, trans-1,4-cyclohexylene substituted with cyano, methyl, fluorine or chlorine, trans-1,4-cyclohexane wherein 2 non-adjacent CH$_2$ groups are replaced by oxygen, unsubstituted 1,4-phenylene, 1,4-phenylene substituted with cyano, methyl, fluorine or chlorine, or 1,4-phenylene having 1 CH group or 2 CH groups replaced by nitrogen.

13. A liquid crystalline mixture according to claim 10, wherein the compound of formula I is in the final mixture in an amount of about 1 to about 70 wt. % of the final mixture.

14. A liquid crystalline mixture according to claim 13, wherein the amount of the compound of formula I in the final mixture is about 3 to about 40 wt. %.

15. In a ferroelectric electro-optical indicating device of the type having a liquid crystalline mixture sandwiched between two transparent plates having polarizers and electrode-means, wherein the improvement comprises:

said liquid crystalline mixture having a positive dielectric anisotropy and containing at least two components wherein at least one component is a compound formula

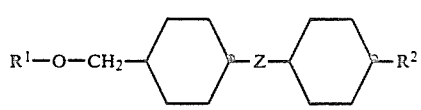 I wherein Z is a single covalent bond or —CH$_2$—CH$_2$—; $R^1$ is alkyl of 1 to 10 carbon atoms or 2-alkenyl of 3 to 10 carbon atoms; and $R^2$ is 1E-alkenyl, 3E-alkenyl, 4-alkenyl, (2-alkenyl)oxymethyl, alkyl or alkoxymethyl having from 1 to 12 carbon atoms; with the proviso that $R^1$ is 2-alkenyl and Z is —CH$_2$CH$_2$— when $R^2$ is alkyl or alkoxymethyl.

* * * * *

UNITED STATES PATENT AND TRADEMARK OFFICE
CERTIFICATE OF CORRECTION

PATENT NO. : 5,102,578
DATED : April 7, 1992
INVENTOR(S) : Richard Buchecker, Martin Schadt and Alois Villiger It is certified that error appears in the above-identified patent and that said Letters Patent is hereby corrected as shown below:

On the title page: Item [30] under Foreign Application Priority Data, please delete "CA Canada" and insert therefor  -- CH Switzerland -- in each instance.

Signed and Sealed this

First Day of June, 1993

Attest:

MICHAEL K. KIRK

*Attesting Officer*   *Acting Commissioner of Patents and Trademarks*